US009564038B2

(12) United States Patent
Wallace et al.

(10) Patent No.: US 9,564,038 B2
(45) Date of Patent: Feb. 7, 2017

(54) METHOD AND APPARATUS FOR IMPROVING HAND-SANITIZING COMPLIANCE IN HEALTH CARE FACILITIES

(71) Applicants: Cynthia K. Wallace, Portland, OR (US); David H. Madden, Portland, OR (US)

(72) Inventors: Cynthia K. Wallace, Portland, OR (US); David H. Madden, Portland, OR (US)

(73) Assignee: Strategic Healthcare Innovations, Portland, OR (US)

( * ) Notice: Subject to any disclaimer, the term of this patent is extended or adjusted under 35 U.S.C. 154(b) by 0 days.

(21) Appl. No.: 14/663,809

(22) Filed: Mar. 20, 2015

(65) Prior Publication Data
US 2016/0275778 A1 Sep. 22, 2016

(51) Int. Cl.
G08B 23/00 (2006.01)
G08B 21/24 (2006.01)
G06F 19/00 (2011.01)

(52) U.S. Cl.
CPC ........... *G08B 21/245* (2013.01); *G06F 19/327* (2013.01)

(58) Field of Classification Search
CPC ...... G08B 21/245; G08Q 10/00; G08Q 10/06; G06F 19/327; G06F 19/3418
USPC .......... 340/10.1, 573.1, 539.12, 539.11, 540, 340/603, 539.13
See application file for complete search history.

(56) References Cited

U.S. PATENT DOCUMENTS

| | | | | |
|---|---|---|---|---|
| 6,727,818 B1* | 4/2004 | Wildman | ............ | G06F 19/3418 340/10.1 |
| 7,782,214 B1* | 8/2010 | Lynn | .................... | G08B 21/245 340/540 |
| 7,898,407 B2* | 3/2011 | Hufton | ...................... | G01S 1/70 222/23 |
| 8,212,653 B1* | 7/2012 | Goldstein | ............ | G08B 21/245 235/375 |
| 8,547,220 B1* | 10/2013 | Dempsey | ............ | G08B 13/1627 340/539.12 |
| 9,147,334 B2* | 9/2015 | Long | ........................ | H04Q 9/00 |
| 2002/0183979 A1* | 12/2002 | Wildman | ............... | G06F 19/327 702/188 |
| 2003/0030562 A1* | 2/2003 | Lane | .................... | G08B 21/245 340/573.4 |
| 2004/0193449 A1* | 9/2004 | Wildman | ............... | G06Q 50/22 705/2 |
| 2005/0035862 A1* | 2/2005 | Wildman | ............... | A61B 5/1113 340/573.1 |
| 2008/0019489 A1* | 1/2008 | Lynn | ........................ | A47K 5/12 379/93.01 |
| 2008/0019490 A1* | 1/2008 | Lynn | ........................ | G07F 9/02 379/93.01 |
| 2008/0021779 A1* | 1/2008 | Lynn | .................... | G06Q 20/206 705/14.65 |
| 2008/0246599 A1 | 10/2008 | Hufton | | |

(Continued)

*Primary Examiner* — Hoi Lau
(74) *Attorney, Agent, or Firm* — Mersenne Law

(57) ABSTRACT

Embodiments of the invention track users' hand-cleaning compliance and display an indication of each user's compliance so that others can estimate how well each user complies with policy guidelines. Making sanitation compliance visible in this way enables social pressure to be focused on negligent users without requiring others to take specific, individual actions to call out a negligent user. Other features of the system are also described and claimed.

5 Claims, 4 Drawing Sheets

(56) References Cited

U.S. PATENT DOCUMENTS

| | | | |
|---|---|---|---|
| 2009/0091458 A1* | 4/2009 | Deutsch | G06F 19/327 340/573.1 |
| 2009/0189759 A1* | 7/2009 | Wildman | G06F 19/3418 340/539.12 |
| 2009/0224907 A1* | 9/2009 | Sinha | G08B 21/245 340/539.11 |
| 2009/0237651 A1* | 9/2009 | Arndt | A01N 25/00 356/229 |
| 2009/0267776 A1* | 10/2009 | Glenn | G08B 21/245 340/573.1 |
| 2010/0134296 A1* | 6/2010 | Hwang | A47K 5/1217 340/573.1 |
| 2010/0164728 A1* | 7/2010 | Plost | G08B 21/245 340/573.1 |
| 2010/0315244 A1* | 12/2010 | Tokhtuev | G06Q 10/00 340/603 |
| 2010/0321180 A1* | 12/2010 | Dempsey | G06Q 10/06 340/539.12 |
| 2010/0328076 A1* | 12/2010 | Kyle | G06F 19/327 340/573.1 |
| 2010/0328443 A1* | 12/2010 | Lynam | G06F 19/327 348/77 |
| 2011/0121974 A1* | 5/2011 | Tenarvitz | G08B 21/245 340/573.1 |
| 2011/0169643 A1* | 7/2011 | Cartner | G08B 21/245 340/573.1 |
| 2011/0206378 A1* | 8/2011 | Bolling | G08B 21/245 398/108 |
| 2011/0273298 A1* | 11/2011 | Snodgrass | G08B 21/245 340/573.1 |
| 2012/0112906 A1* | 5/2012 | Borke | G06F 19/327 340/539.13 |
| 2012/0194338 A1* | 8/2012 | Snodgrass | G08B 21/245 340/539.12 |
| 2012/0256742 A1* | 10/2012 | Snodgrass | G06F 19/327 340/539.12 |
| 2013/0027199 A1* | 1/2013 | Bonner | G08B 21/24 340/539.11 |
| 2013/0113619 A1* | 5/2013 | Snodgrass | G07C 11/00 340/539.11 |
| 2013/0122807 A1* | 5/2013 | Tenarvitz | H04B 5/0031 455/41.1 |
| 2013/0127615 A1* | 5/2013 | Snodgrass | G05B 1/01 340/539.13 |
| 2014/0070950 A1* | 3/2014 | Snodgrass | G06F 19/327 340/573.5 |
| 2014/0180713 A1* | 6/2014 | Tenarvitz | G06F 19/327 705/2 |
| 2014/0327545 A1* | 11/2014 | Bolling | G08B 21/245 340/573.1 |
| 2014/0375457 A1 | 12/2014 | Diaz | |
| 2016/0275778 A1* | 9/2016 | Wallace | G08B 21/245 |

* cited by examiner

METHOD AND APPARATUS FOR IMPROVING HAND-SANITIZING COMPLIANCE IN HEALTH CARE FACILITIES

CONTINUITY AND CLAIM OF PRIORITY

This is an original U.S. patent application.

FIELD

The invention relates to electronic communication, monitoring and data collection systems having a personal, portable component and a fixed component which interact to obtain time, location and activity information. More specifically, the invention relates to systems for monitoring and displaying indications of human behavior to others, to engage social pressure for improving compliance with behavioral guidelines and requirements.

BACKGROUND

Healthcare procedures, facilities, equipment and knowledge have advanced rapidly and significantly over the centuries. Patient outcomes have improved, and many injuries and diseases that would have been fatal in earlier times are now treated and cured as a matter of course.

These changes in prognosis for the most serious maladies cause a reshuffling among other causes and contributors to death and disease. When injuries themselves were commonly fatal, differences in sterilization and sanitation procedures were relatively inconsequential. Now that many injuries can be treated effectively, though, infections acquired during treatment and convalescence can turn out to be a significant factor in overall outcomes. This is especially true of hospital-acquired infections: because hospital facilities, personnel and patients experience increased antibacterial procedures (e.g., autoclaving, hand-washing and antibiotic courses), bacterial populations there are subjected to strong selection pressure, and difficult-to-treat infections have become more common.

These "superbug" pathogens (e.g., Methicillin-resistant *Staphylococcus aureus*, "MRSA") can be spread among hospital patients by improperly- or inadequately-sanitized equipment, but a common vector is the hands of healthcare providers, who may touch or handle patients or equipment, then inadvertently transfer pathogens an uninfected patient by neglecting to follow recommended or required hand-sanitation procedures.

Hand sanitation compliance is known to be an effective target for hospital process improvement. Studies often show compliance rates below 50%. Prior-art approaches to improve compliance tend to fall into two classes: education (via seminars, personnel directives, "reminder" posters and literature, etc.) and technological (via interlocks connecting sanitation activity to premises access—e.g., a door lock will not open unless the sanitation procedure is completed). Technological approaches tend to be expensive, complicated and inconvenient in direct proportion to their reliability; no such approach is widely adopted and successful. Education is inexpensive, but of limited efficacy against habitual offenders.

An inexpensive approach that is less intrusive but more effective may be of significant value in this field.

SUMMARY

Embodiments of the invention provide a visual indicator of the hand-hygiene compliance of one person to other people in the facility. Thus, instead of acting simply as a reminder to the person, an embodiment makes the person's compliance (or non-compliance) visible to others, thus engaging social pressure to encourage compliance. Embodiments make a normally-inconspicuous, -hidden, -out-of-sight or -invisible behavior visible or otherwise noticeable or trackable, so that everyone (or at least appropriate individuals or monitoring systems, as the case may be) can easily tell who is not washing his hands properly.

DETAILED DESCRIPTION

Figure 1:
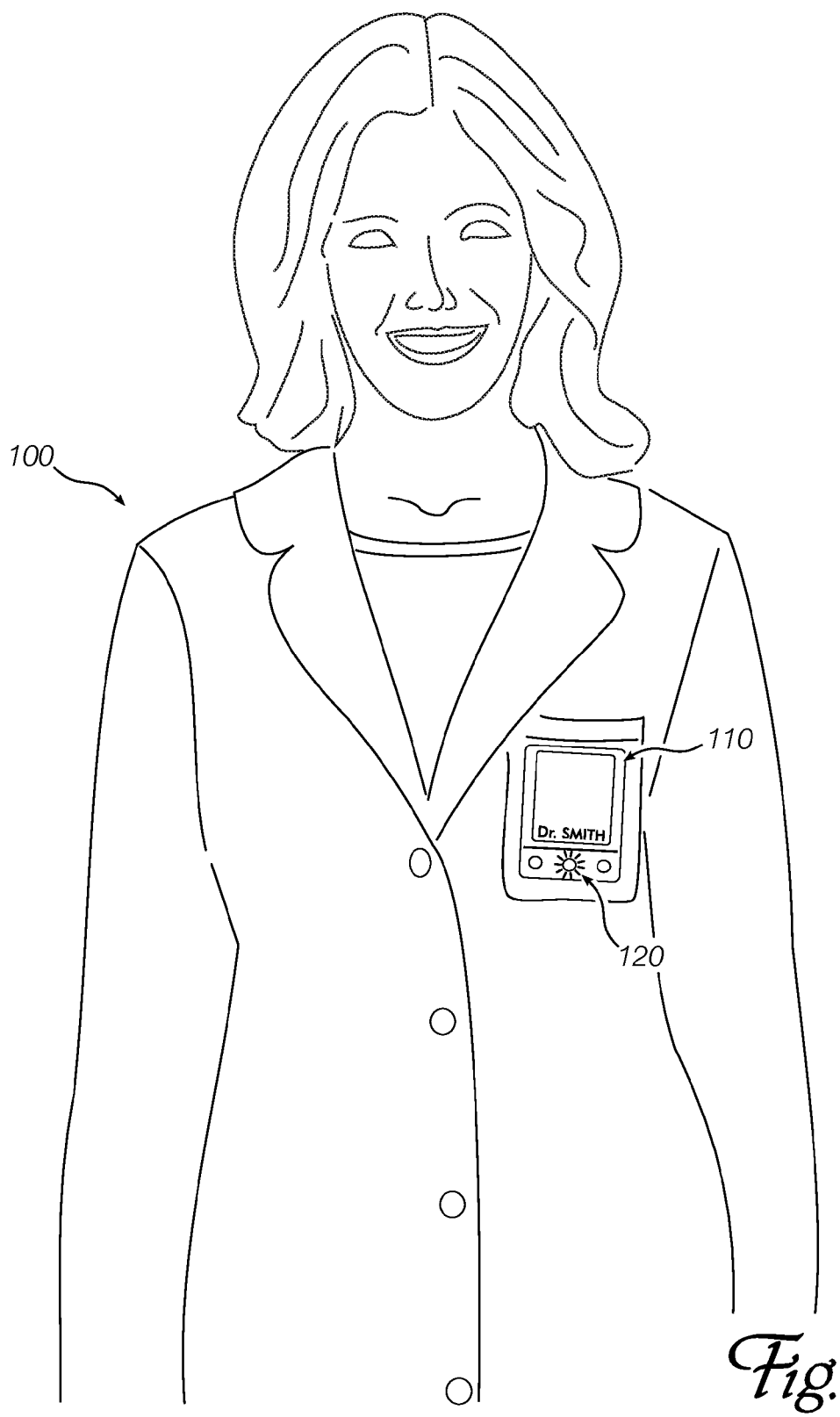
FIG. 1 shows a healthcare professional wearing an identification badge that includes an embodiment of the invention.

FIG. 1 shows a doctor 100 wearing an identification badge 110 that includes an embodiment of the invention. Identification badges are commonly worn by authorized personnel in healthcare facilities while they are on duty, so the inventive system integrates well with existing equipment and procedures. Most embodiments include a light 120 or other visible indicator that is activated as described below. However, an embodiment might use a color-changing display or an audible signal instead of an illuminated light. The only requirement is that the device can communicate a modest amount of information to other people or systems that encounter or interact with the embodiment.

The "badge" portion of the inventive system is the most visible part, but the system depends on one or two other components as well. One other component is a wireless transmitter that is preferably integrated into a hand-sanitization device such as a soap or sanitizer dispenser, or a hand-washing sink. When the hand-sanitization device is used, the wireless transmitter transmits a message to a nearby badge, which updates its state as discussed below. The wireless transmitter may use a radio signal, a light signal (either visible or infrared light), or a sound signal (either an audible tone or pattern, or an ultrasonic tone or pattern). The badge portion of the system comprises a receiver to receive the signal from the wireless transmitter.

Another component that is present in some embodiments is a wireless transmitter that is not causally associated with a hand-sanitization device—it transmits a signal based on other events or conditions, or even a continuous signal. This component is called an "arming" transmitter. A badge that receives a signal from an arming transmitter responds as discussed below.

Figure 2:
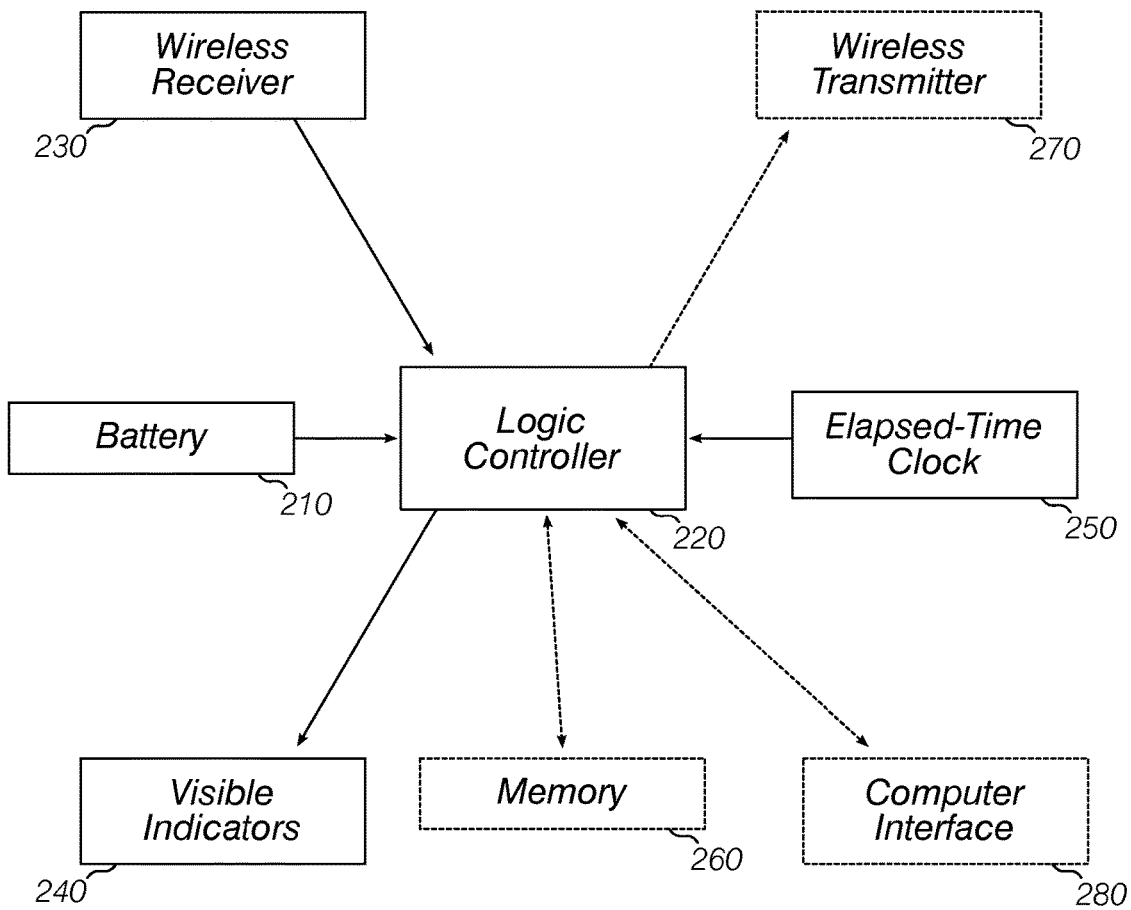
FIG. 2 is a block diagram of elements of the "badge" portion of an embodiment.

FIG. 2 is a block diagram showing components of the badge portion of an embodiment. Most badges are self-powered, so they include a battery 210. A rechargeable battery is preferred. The battery supplies power to a logic controller 220, such as an electronic microcontroller. This component detects signals received by the wireless receiver 230 and implements the logic outlined in the flow chart of FIG. 4. Wireless receiver 230 may be a radio receiver, a visible-light or infrared receiver, or an audio receiver, according to the transmission type in use by the system. A badge also includes one or more visible indicators 240, such as LED lights shown in FIG. 1 at 120, electroluminescent panels, liquid-crystal displays or the like. The visible indicator displays information to viewers as directed by the logic controller 220. It is not necessary that the person wearing this portion of an embodiment can see his own visible indicators, but it is not necessary to hide the state of the indicators from this person either. Some embodiments may display information in an invisible or coded form, which requires special equipment to perceive or understand. For example, instead of visible LEDs, an embodiment could flash an infrared signal that is only visible to a special camera or receiver. Or an electroluminescent display could present a machine-readable pattern that can be decoded by a bar-code or QR-code scanner.

Embodiments include an elapsed-time clock 250. This may be a realtime clock (i.e., the embodiment may be able to coordinate its actions to wall-clock time) or it may be a simple counting timer for measuring the time elapsed since a previous event. Most embodiments will also include at least a small amount of digital memory 260 for recording the times at which various events occurred. Some embodiments may also include a wireless transmitter 270, which is preferably of the same type as the hand-sanitizer and arming transmitters. If a wireless transmitter is included, one badge device can communicate directly with another badge, or with other devices participating in the system.

Some badges also include a computer interface, such as a Universal Serial Bus ("USB") interface. This can allow the badge to upload information it collected during use: when the wearer washed his hands (or the intervals between hand washings); the identity and/or location of the hand-washing stations used; and possibly the identities of other workers/badges encountered during the day. An analysis program can thus track hand-washing compliance rates and similar metrics and determine whether the system is succeeding in increasing compliance. The information can also be useful for forensic analysis of infection outbreaks, as discussed below. A computer interface may also be useful for configuring the badge by sending timeout patterns, instructions to collect certain types of information, or software to allow the badge to interact with new types of devices.

Figure 3:
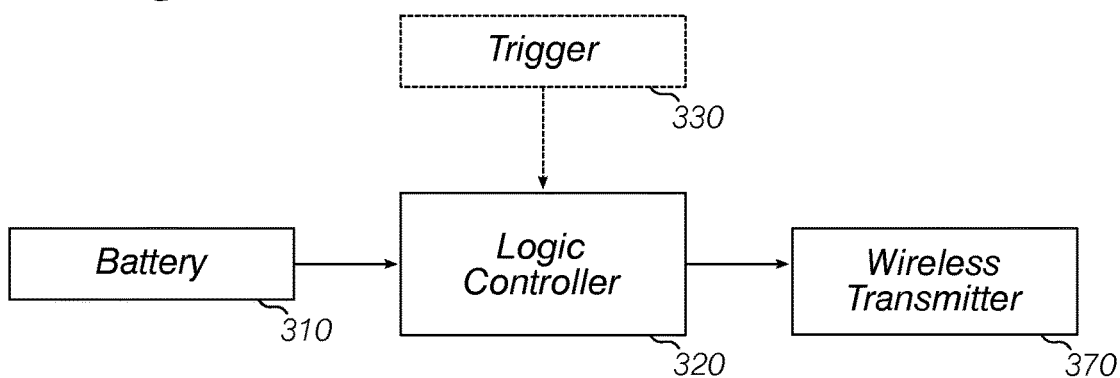
FIG. 3 is a block diagram of elements of the "sanitizer" or "arming transmitter" portions of an embodiment.

FIG. 3 is a block diagram of components of the hand-sanitizer and/or "arming transmitter" portions of an embodiment. These devices are somewhat simpler than the badge portion because they need not include either an elapsed-time clock or a visual indicator. (They may include both, of course; in fact, in some embodiments, the "badge" hardware can be repurposed as a "sanitizer" or "arming transmitter" merely by changing its software.) The transmitters include a battery 310, a logic controller 320 and a wireless transmitter 370. They may also include a trigger 330, which causes the control logic to send a wireless message at a particular time (e.g., after activation of a hand-sanitization mechanism) rather than sending the message continuously.

Figure 4:
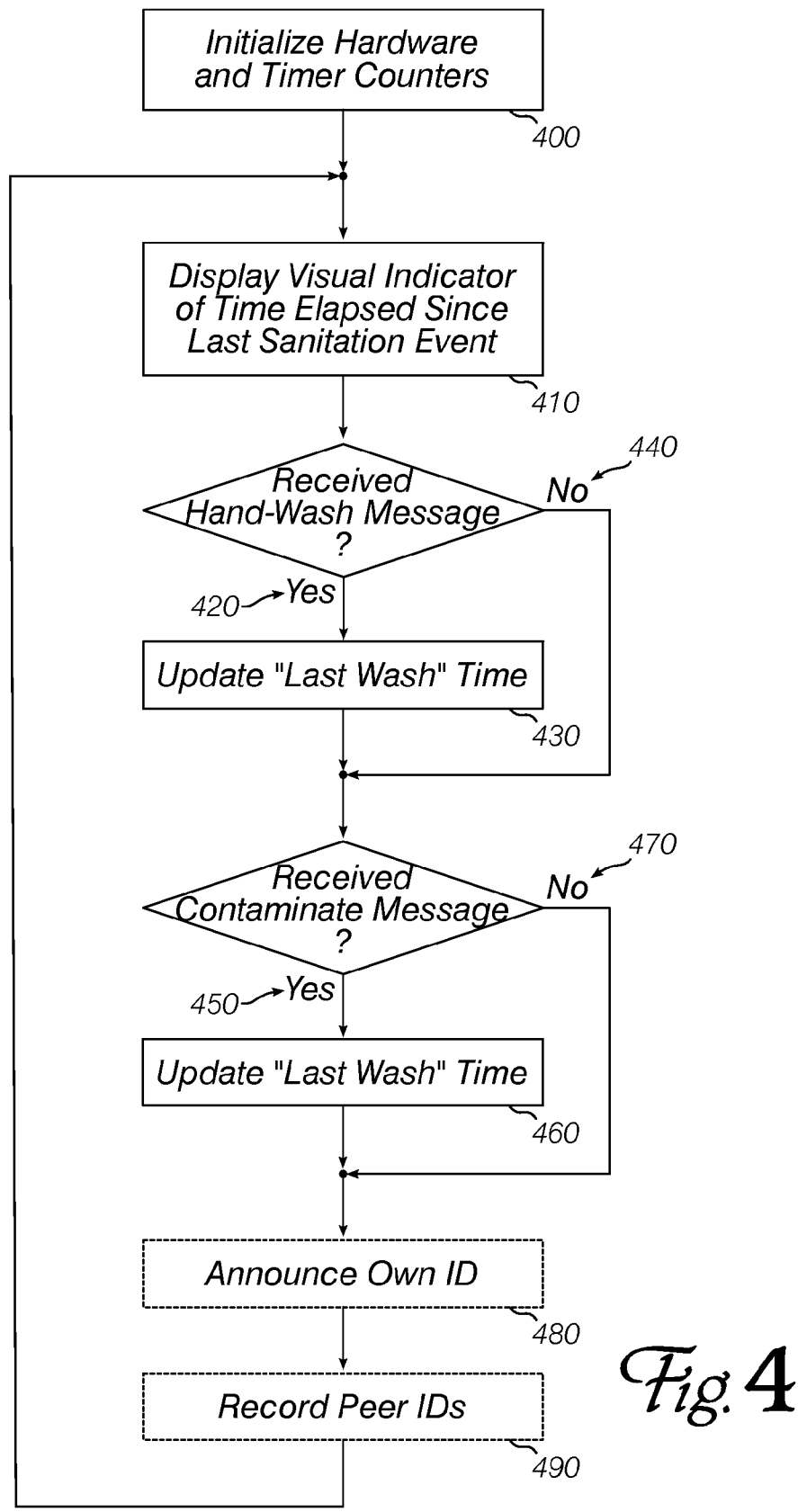
FIG. 4 is a flow chart outlining some operations according to an embodiment.

FIG. 4 outlines the logic of the badge: first, hardware systems and elapsed-time counters are initialized (400). Once initialized, the logic controller repeatedly performs operations comprising displaying a visual indicator of time elapsed since the last sanitation event (410). The logic checks for newly-received "hands washed" messages (e.g., from a hand-sanitizer transmitter), and if one was received (420), the "last sanitation event" time is updated (430). Next (or if no "hands washed" message was received, 440), the logic checks for messages received from an arming transmitter. (For reasons discussed presently, these messages may be considered "contaminate" messages.) If a "contaminate" message was received (450), the "last wash" time is updated (460) by increasing the elapsed time since last wash. Finally (and/or if no "contaminate" message was received, 470), embodiments that include a wireless transmitter may transmit their own identification (480), and may also record any peer identifications received from other badge units (490).

In practical effect, the badge portion of an embodiment displays a visual indication that allows viewers to estimate the amount of time that has elapsed since the badge wearer last washed his or her hands. When the badge receives a message from a hand-washing or hand-sanitation transmitter, it sets an elapsed-time counter to zero—the healthcare provider just washed his hands. This counter increases while the person does his work, and the visual indicator changes to show the increasing time. For example, green LEDs might blink rapidly and/or brightly just after washing, then slow down or dim as time passes.

Eventually, the visual indicator will change to show that even more time has elapsed since the person last washed his hands. For example, green LEDs may stop blinking, and red LEDs may start blinking instead. This indicates that an improbably long amount of time has elapsed since the provider washed his hands. The timeout periods of a system are configurable. Typically, at least three different time periods will be visually distinguishable: a first period immediately following hand sanitation, a second, reasonable period thereafter, and a third period which is considered "too long" since the last hand sanitation. The visual indicator may also show events like "hand wash detected," "message from peer badge received," or "battery low." The typical time from "freshly washed hands" to "must wash hands again" may be set to the same order of magnitude as a patient exam. In a representative installation, this may be about 10 minutes. (In certain fields, longer or shorter timeout periods may be more convenient. Some systems may have badges with different timeouts for use by different healthcare providers, whose activities and patient interactions are different from one another.)

Figure 5:
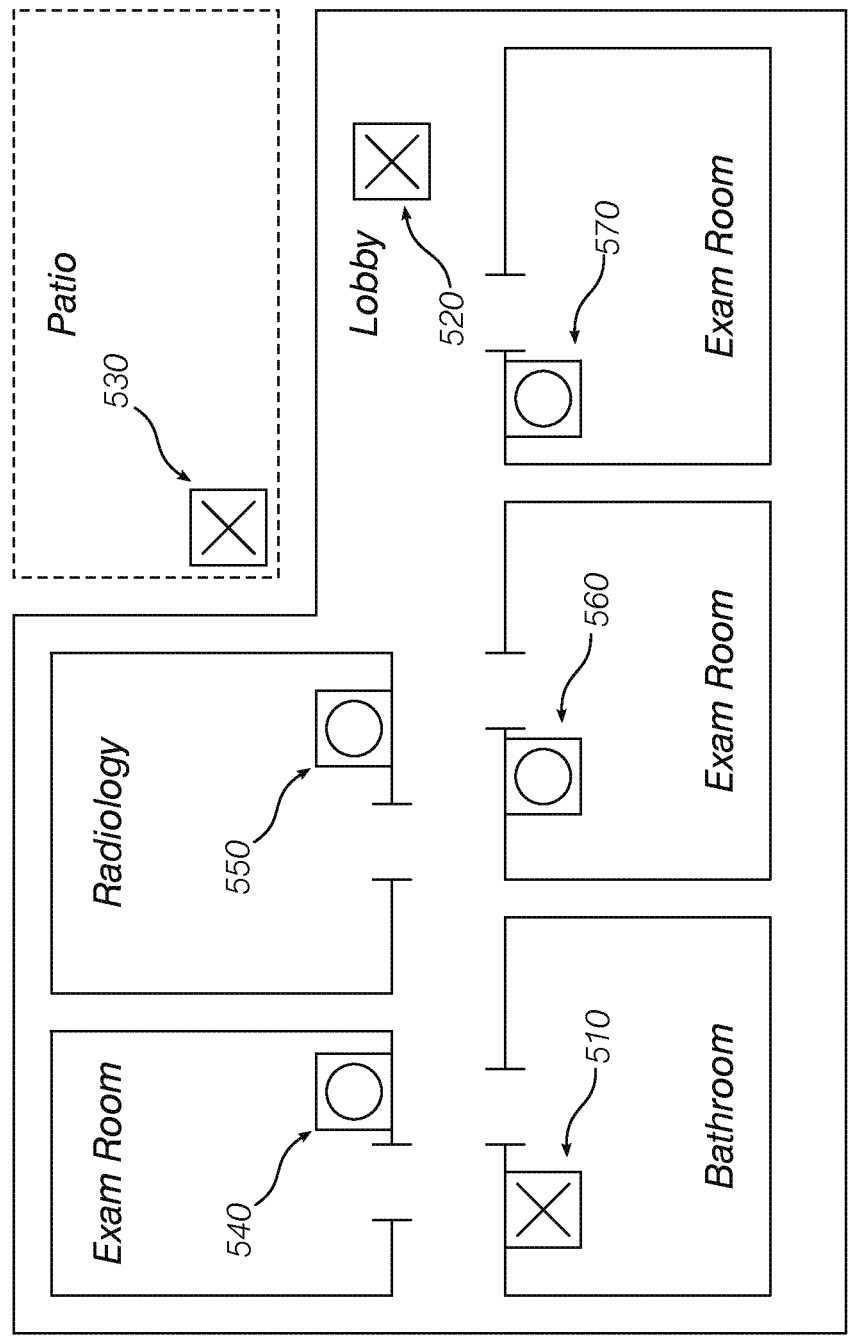
FIG. 5 shows a sample facility layout with possible location for sanitizer dispensers and arming stations.

In installations comprising arming transmitters, the message from the arming transmitter causes badges that receive the message to immediately adjust their elapsed-time counters. Often, the adjustment corresponds to an increase in elapsed time since the last hand-sanitation event, which means (for example) that the visual indicator will start blinking red sooner than it would otherwise. This can be used to "discharge" the hand-cleanliness indication of a badge when the wearer enters or exits a location where contamination is deemed likely. For example, arming transmitters may be installed in a bathroom or lavatory facility (FIG. 5, 510), so that personnel leaving the bathroom will soon (or immediately) display a blinking red badge until they wash their hands again. Other locations may also be "armed" this way: for example, a lobby 520 or an uncontrolled space (e.g., a cafeteria or outdoors plaza 530) may be set so that personnel returning from these areas must immediately wash their hands, lest they be seen by others as neglecting their hygiene duties. Hand-sanitation transmitters may be stationed, for example, in exam rooms and other convenient locations (540, 550, 560).

An installation deploying badges and transmitters according to embodiments of the invention may include an "education" component: posters or literature directed at patients and visitors may encourage them to check their providers' badges for the "Green is Clean" signal, and speak up if someone's badge is blinking red.

It is appreciated that when badges can communicate with each other, they can record the identities of other badges they encounter (as well as the times, sequences and/or locations of such encounters). This information can be uploaded to an analysis system, for example while the badges are being recharged. The information may be useful in forensic analysis of the spread of a hospital-acquired infection: it can help analysts determine who was "patient zero," and how the infection was communicated from that patient, through a chain of patient and provider encounters to others.

In a preferred embodiment, the hardware and control software of an embodiment are implemented as an identification badge holder that can be suspended from a worker by a lanyard or attached to clothing via a clip, pin or magnet system. In some instances, the electronics and power supply of an embodiment may be separable from the badge holder so that the battery can be more easily recharged, and so that data collected by the device can be uploaded to an analysis system. In other embodiments, the display device may have identification information printed directly upon it, so that it serves as an identification badge in itself. Other conventional identification-badge functions may be combined with the inventive indicators and control logic.

An embodiment of the invention may be a machine-readable medium, including without limitation a non-transient machine-readable medium, having stored thereon data and instructions to cause a programmable processor to perform operations as described above. In other embodiments, the operations might be performed by specific hardware components that contain hardwired logic. Those operations might alternatively be performed by any combination of programmed computer components and custom hardware components.

Instructions for a programmable processor may be stored in a form that is directly executable by the processor ("object" or "executable" form), or the instructions may be stored in a human-readable text form called "source code" that can be automatically processed by a development tool commonly known as a "compiler" to produce executable code. Instructions may also be specified as a difference or "delta" from a predetermined version of a basic source code. The delta (also called a "patch") can be used to prepare instructions to implement an embodiment of the invention, starting with a commonly-available source code package that does not contain an embodiment.

In some embodiments, the instructions for a programmable processor may be treated as data and used to modulate a carrier signal, which can subsequently be sent to a remote receiver, where the signal is demodulated to recover the instructions, and the instructions are executed to implement the methods of an embodiment at the remote receiver. In the vernacular, such modulation and transmission are known as "serving" the instructions, while receiving and demodulating are often called "downloading." In other words, one embodiment "serves" (i.e., encodes and sends) the instructions of an embodiment to a client, often over a distributed data network like the Internet. The instructions thus transmitted can be saved on a hard disk or other data storage device at the receiver to create another embodiment of the invention, meeting the description of a non-transient machine-readable medium storing data and instructions to perform some of the operations discussed above. Compiling (if necessary) and executing such an embodiment at the receiver may result in the receiver performing operations according to a third embodiment.

In the preceding description, numerous details were set forth. It will be apparent, however, to one skilled in the art, that the present invention may be practiced without some of these specific details. In some instances, well-known structures and devices are shown in block diagram form, rather than in detail, in order to avoid obscuring the present invention.

Some portions of the detailed descriptions may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "processing" or "computing" or "calculating" or "determining" or "displaying" or the like, refer to the action and processes of a computer system or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, including without limitation any type of disk including floppy disks, optical disks, compact disc read-only memory ("CD-ROM"), and magnetic-optical disks, read-only memories (ROMs), random access memories (RAMs), erasable, programmable read-only memories ("EPROMs"), electrically-erasable read-only memories ("EEPROMs"), magnetic or optical cards, or any type of media suitable for storing computer instructions.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will be recited in the claims below. In addition, the present invention is not described with reference to any particular programming language. It will be appreciated that a variety of programming languages may be used to implement the teachings of the invention as described herein.

The applications of the present invention have been described largely by reference to specific examples and in terms of particular allocations of functionality to certain hardware and/or software components. However, those of skill in the art will recognize that social pressure can be engaged by making invisible behaviors visible to other people via software and hardware that distribute the functions of embodiments of this invention differently than herein described. Such variations and implementations are understood to be captured according to the following claims.

We claim:

1. A hand-sanitizing compliance improving system, comprising:
   a hand-sanitizing station having a wireless transmitter operative to transmit a first signal when the hand-sanitizing station is operated by an individual;
   an arming station having a wireless transmitter operative to transmit a second signal to receivers in a vicinity of the arming station; and
   a hand-sanitizing compliance monitor having a wireless receiver operative to receive the first signal from the hand sanitizing station and the second signal, wherein
   the hand-sanitizing compliance monitor is adapted to be carried by the individual,
   the hand-sanitizing compliance monitor emits a perceptible indication of an elapsed time since the wireless receiver last received the first signal from the hand sanitizing station, and
   the hand-sanitizing compliance monitor adjusts the elapsed-time to emit the perceptible indication upon receiving the second signal,
   the hand-sanitizing compliance monitor further comprising:
   a wireless transmitter operative to transmit an encounter signal to a second hand-sanitizing compliance monitor, wherein
   the second hand-sanitizing compliance monitor records a time at which it received the encounter signal.

2. The hand-sanitizing compliance improving system of claim 1, wherein the perceptible indication includes a first distinguishable indication corresponding to a first time period immediately following the transmission and reception of the signal,
   a second distinguishable indication corresponding to a second time period following the first time period, and
   a third distinguishable indication corresponding to a third time period following the second time period.

3. The hand-sanitizing compliance improving system of claim 1 wherein the signal is a radio signal.

4. The hand-sanitizing compliance improving system of claim 1 wherein the signal is an infrared light signal.

5. The hand-sanitizing compliance improving system of claim 1, further comprising:
   a database to record signal reception times from a plurality of hand-sanitizing compliance monitor devices.

* * * * *